United States Patent [19]

Hansen, Jr. et al.

[11] Patent Number: 4,510,085
[45] Date of Patent: Apr. 9, 1985

[54] ANTIHYPERTENSIVE TETRAPEPTIDE AMIDES

[75] Inventors: Donald W. Hansen, Jr., Chicago; Stamatios Papaioannou, Morton Grove, both of Ill.

[73] Assignee: G.D. Searle & Co., Skokie, Ill.

[21] Appl. No.: 599,313

[22] Filed: Apr. 12, 1984

[51] Int. Cl.³ .............................................. C07C 103/52
[52] U.S. Cl. ........................ 260/112.5 E; 260/112.5 R
[58] Field of Search ................... 260/112.5 E, 112.5 R

[56] References Cited

U.S. PATENT DOCUMENTS 4,273,704 6/1981 Mazur ........................... 260/112.5 E

OTHER PUBLICATIONS

Goodman & Gilman, *The Pharmacological Basis of Therapeutics*, (New York, 1975), Fifth Edition, Chaps. 26, 27, 28, 30, 33, 39, 40.

Poulsen, Burton, & Haber, "Competitive Inhibitors of Renin," *Biochemistry*, 12, 3877-3882 (1973).

Burton, Cody, Herd, & Haber, "Specific Inhibition of Renin by an Angiotensinogen Analog . . . ", *Proc. Natl. Acad. Sci. USA*, 77, 5476-5479 (1980).

Cody, Burton, Evin, Poulsen, Herd, & Haber, "A Substrate Analog Inhibitor of Renin that is Effective in Vivo", *Biochem. Biophys. Res. Commun.*, 97, 230-235 (1980).

Burton, Poulsen, & Haber, "Competitive Inhibitors of Renin . . . ", *Biochemistry*, 14, 3892-3898 (1975).

Haas, Lewis, Scipione, & Koshy, "Micromethod for the Assay of Renin of Seven Species," *Hypertension*, 1, 112-117 (1979).

Eddy & Leimbach, "Synthetic Analgesics. II . . . ", *J. Pharmacol. and Exp. Therap.*, 107, 385-393 (1953).

*Primary Examiner*—Delbert R. Phillips
*Attorney, Agent, or Firm*—John J. McDonnell

[57] ABSTRACT

This invention relates to novel tetrapeptide adamantyl amides that are useful in the treatment of hypertension.

40 Claims, No Drawings

ANTIHYPERTENSIVE TETRAPEPTIDE AMIDES

BACKGROUND OF THE INVENTION (a) Field of the Invention

This invention relates to novel tetrapeptide amides of Formula I that are useful in the treatment of hypertension.

Hypertension is a condition caused by any of a variety of functional abnormalities. For example, hypertension may be related to abnormalities in adrenergic, cholinergic, or neuromuscular interactions; in hormonal balance; or in kidney function, which malfunctions often are caused by abnormalities of the other systems. Treatment with drugs that are intended to act at some receptor site involved in one of the malfunctioning systems has frequently been the basis of therapy. For example, numerous neural receptor blockers are known to act as antihypertensive agents, and diuretics are commonly used to counteract the effects of fluid retention associated with kidney dysfunction. Each of these regimens, however, is associated with side effects often related to inadequate specificity. See generally L. S. Goodman and A. Gilman, eds. *The Pharmacological Basis of Therapeutics* (New York, 1975), Fifth Edition, Chaps. 26, 27, 28, 30, 33, 39, 40.

The renin-angiotensin system has been implicated in hypertension. See Goodman and Gilman, supra, pp. 630–637. The enzyme renin converts the plasma protein angiotensinogen to the essentially inactive decapeptide angiotensin I, which in turn is proteolytically converted by the so-called "converting enzyme" to the potently vasoactive octapeptide angiotensin II. Various peptidases further hydrolyze angiotensin II to essentially inactive peptide fragments. In addition to regulating blood pressure, angiotensin also stimulates the secretion of aldosterone and thus is intimately involved in regulating the sodium-potassium balance. Thus, inhibition of renin could be an important means of controlling high blood pressure. Certain short-chain peptide analogs of angiotensinogen segments have been reported to inhibit renin activity. K. Poulsen, J. Burton, and E. Haber, *Biochemistry*, 12, 3877–3882 (1973); J. Burton, K. Poulsen, and E. Haber, *Biochemistry*, 14, 3892–3898 (1975); J. Burton, R. J. Cody, Jr., A. J. Herd, and E. Haber, *Proc. Natl. Acad. Sci. U.S.A.*, 77, 5476–5479 (1980). Peptide inhibitors of renin activity have also been reported to lower blood pressure in primates. See J. Burton, R. J. Cody, Jr., A. J. Herd, and E. Haber, *Proc. Natl. Acad. Sci. U.S.A.*, 77, 5476–5479 (1980); R. J. Cody, J. Burton, G. Evin, K. Poulsen, J. A. Herd, and E. Haber, *Biochem. Biophys. Res. Commun.*, 97, 230–235 (1980). The present invention provides peptide amides of shorter length which are renin inhibitors and exhibit antihypertensive activity.

(b) Prior Art

Certain N-adamantane-substituted tetrapeptide amides are known. U.S. Pat. No. 4,273,704, having the same assignee as the present invention, relates to analgesic tetrapeptide amides having optionally substituted tyrosine as the N-terminal amino acid residue. Although the tyrosine-containing compounds disclosed in the '704 patent have been discovered by the present inventors to exhibit renin inhibitory activity, the antihypertensive activity has not previously been disclosed for those compounds. Moreover, the compounds of the present invention exhibit significantly less analgesic activity than prior art compounds of the '704 patent, thus affording an unexpected separation of biological properties.

SUMMARY OF THE INVENTION

The invention relates to compounds of Formula I:

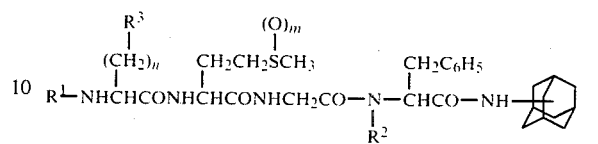

wherein $R^1$ is:
(a) hydrogen; or
(b) alkyl of 1 to 6 carbon atoms, inclusive;
wherein $R^2$ is:
(a) hydrogen; or
(b) alkyl of 1 to 6 carbon atoms, inclusive;
wherein $R^3$ is:

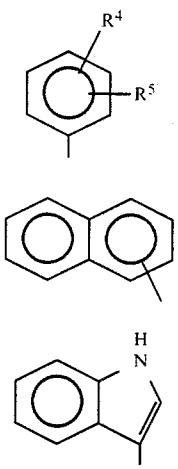

wherein $R^4$ and $R^5$, each being the same or different, are:
(a) hydrogen;
(b) alkyl of 1 to 6 carbon atoms, inclusive; or
(c) halogen;
wherein m is 0, 1 or 2;
wherein n is 0 or an integer of from 1 to 4; and the pharmaceutically acceptable salts thereof.

Examples of alkyl of 1 to 6 carbon atoms, inclusive, are methyl, ethyl, propyl, butyl, pentyl, hexyl, and the isomeric forms thereof, generally referred to as alkyl.

Examples of halogen are fluorine, chlorine, bromine, and iodine.

Examples of pharmacologically acceptable acid addition salts include the hydrochloride, hydrobromide, hydroiodide, sulfate, phosphate, acetate, propionate, lactate, maleate, malate, succinate, and tartrate salts.

DESCRIPTION OF THE INVENTION

The compounds of this invention may be prepared by any number of methods known to those skilled in the art. For example, the particular sequence of reactions by which the individual amino acids are joined to form the compounds of Formula I is generally not of critical importance, being chosen principally for convenience or for maximum yields. Moreover, the choice of activating reagents and conditions for joining amino acids or small peptides is not limited to those specifically described herein. Peptide intermediates and products of this invention are typically purified by crystallization, where possible, or by column chromatography. Furthermore, where racemic amino acid starting materials are employed, intermediates and products may be separated during chromatography into diastereomers. The accompanying Schemes are used to illustrate one of the possible methods used to prepare the compounds of this invention.

Scheme A illustrates a general method for forming intermediates useful in the synthesis of compounds of Formula I.

SCHEME A

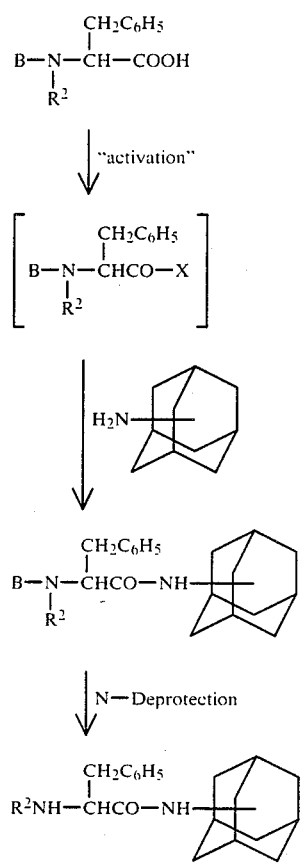

Partially blocked amino acids of Formula II, in which B represents common N-protecting groups such as t-butoxycarbonyl, may be activated by any of several methods known to those skilled in the art. The generally preferred method includes forming a mixed anhydride by reaction with an alkyl chlorocarbonate in an unreactive solvent containing a tertiary amine. Preferred conditions include cooling a mixture of the appropriate compound of Formula II in cold (ca. −30° to −40°) dimethylformamide or dichloromethane containing N-methylmorpholine, followed by addition of isobutyl chloroformate. Once the mixed anhydride of Formula III (X=OCOOCH$_2$CH(CH$_3$)$_2$) has formed, 1- or 2-aminoadamantane (Formula IV) is added and the reaction allowed to proceed at room temperature, giving the fully blocked intermediate of Formula V.

An alternative method of activation employing carbodiimide activation may also be employed to prepare compounds V. For this method, compounds of Formulas III and IV are stirred together in an unreactive solvent, such as dichloromethane, to which is then added a carbodiimide, such as dicyclohexylcarbodiimide. The isolated intermediates, Formula V, are used exactly the same as those formed by the mixed anhydride method.

Using methods appropriate for the particular protecting group B, compounds of Formula V may readily be deprotected to give compounds of Formula VI. Where the t-butoxycarbonyl protecting group is used, for example, preferred deblocking conditions include acid solvolysis in acetic acid containing hydrogen chloride-dioxane. Typically, the resulting hydrochloride salts may be used in subsequent reactions without first isolating the free amine.

Scheme B illustrates one method for extending the peptide chain to form intermediates of Formula XII.

SCHEME B

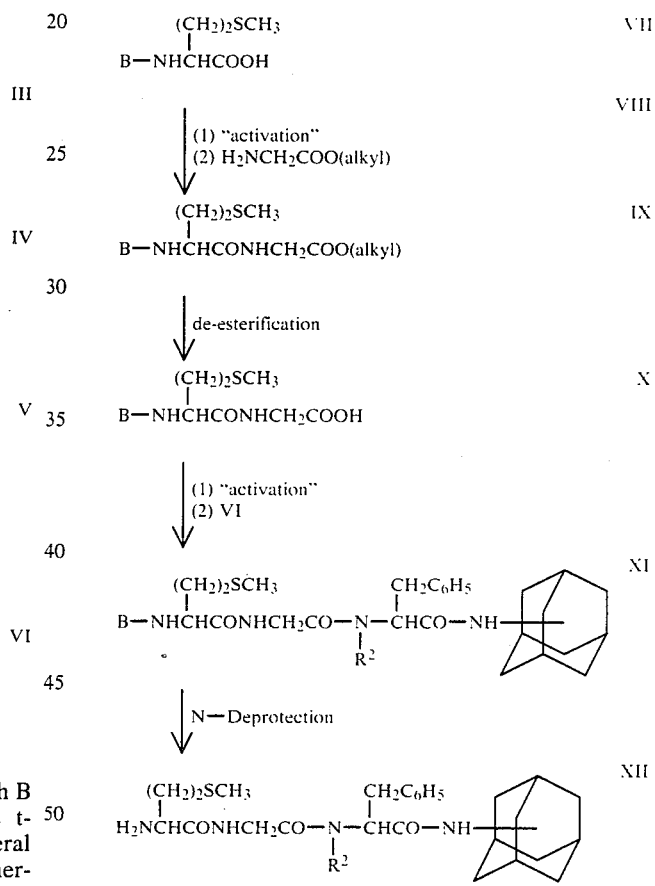

Using methods described above and illustrated in Scheme A, fully protected intermediates of Formula IX are formed from N-protected D-methionine, Formula VII, and glycine esters, Formula VIII. Hydrolysis of these intermediates, Formula IX, affords the analogous acids of Formula X. Preferred hydrolysis conditions include approximately two-fold potassium hydroxide in aqueous tetrahydrofuran, followed by neutralization with sodium bisulfate. Using the methods described above, compounds of Formula X are activated and then coupled with intermediates of Formula VI to form protected peptides of Formula XI. As described above and illustrated in Scheme A, removal of protecting groups B affords amino compounds of Formula XII.

Scheme C illustrates one method for completing the extension of the peptide chains.

SCHEME C

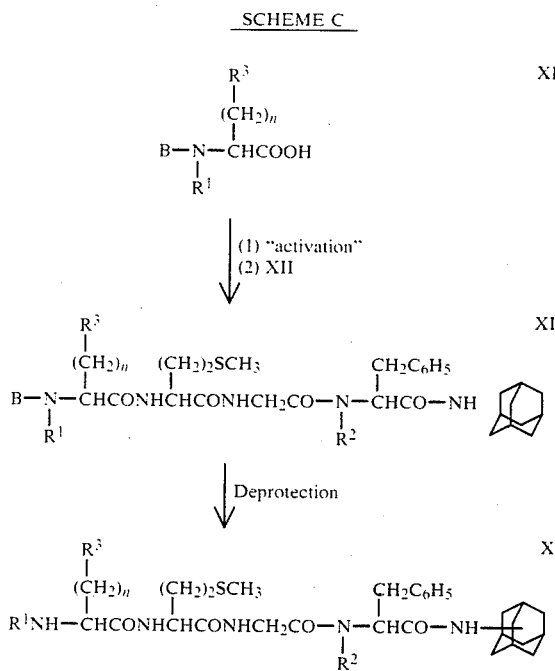

As described above and illustrated in Schemes A and B, suitably protected aromatic amino acids of Formula XIII are activated, for example by using mixed anhydride or carbodiimide methods, and allowed to react with intermediates of Formula XII. Appropriate removal of protecting groups from the resultant compounds of Formula XIV affords compounds of this invention, Formula XV (i.e., Formula I wherein m=0).

Scheme D illustrates one method for preparing sulfoxide or sulfone members of this invention, Formula XVI (i.e., Formula I wherein m=1 or m=2, respectively), which for practical reasons are generally prepared after methionine-containing peptides of Formula XV have been fully formed as described above. Preferred oxidizing conditions include hydrogen peroxide in aqueous methanol-at room temperature, sulfoxides are the predominant or sole oxidation product, whereas at elevated temperatures (e.g., refluxing solvent), sulfones are formed.

SCHEME D

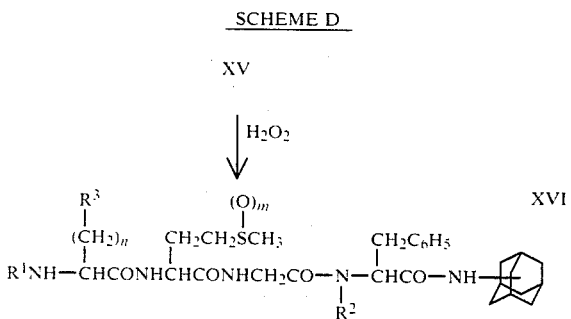

The preferred embodiments of this invention include compounds of the following general structure, Formula XVII.

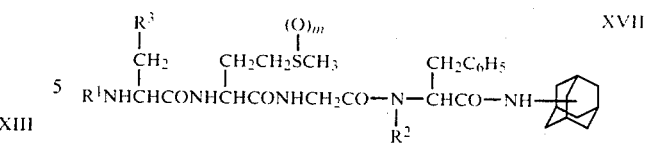

More specifically, the preferred embodiments include compounds of Formula XVII wherein $R^1$ and $R^2$ are separately or together hydrogen or lower alkyl; $R^3$ is optionally substituted phenyl or naphthyl; and m is either 0 or 1.

The most preferred embodiments of this invention include compounds of the following general structure, Formula XVIII.

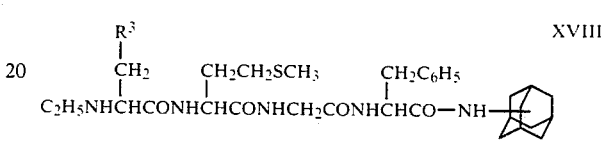

More specifically, the most preferred embodiments include compounds of Formula XVIII wherein $R^3$ is optionally substituted phenyl.

The preferred embodiments illustrated in Examples 15, 16, 25, 29, 33, and 39, below, possess renin inhibition activity, but exhibit significantly lower opiate receptor binding than prior art compounds of U.S. Pat. No. 4,273,704 (i.e., where $R^3$ is optionally substituted 4-hydroxyphenyl).

The renin inhibition activity of the compounds of this invention illustrated in the examples was tested by the following method. Pepstatin and the octapeptide prolylhistidylprolylphenylalanylhistidylleucylphenylalanylvalyltyrosine (or, "Pro-[Phe6]octapeptide"; see J. Burton, K. Poulsen, and E. Haber, *Biochemistry*, 14, 3892–3898 (1975)) are active in this assay.

Inhibition of Human Renin

International reference standard human renin, isolated from kidneys, was obtained from the World Health Organization International Laboratory for Biological Standards (National Institute for Biological Standards and Control, London, England). Renin activity is defined in "Goldblatt units" (GU), the quantity that, when injected directly into the blood stream of an unanesthetized dog, raises the direct mean femoral artery blood pressure by 30 mm Hg in about two minutes. E. Haas, L. Lewis, P. Scipione, and T. J. Koshy, *Hypertension*, 1, 112–117 (1979). Human angiotensinogen was used as an unisolated component of human blood plasma. The enzyme inhibition assay, see K. Poulsen, J. Burton, and E. Haber, *Biochemistry*, 12, 3877–3882 (1973), involved a two-hour incubation at 37° C. of the following final concentrations of reagents (0.25 ml total volume): 0.1 mGU/ml human renin; 0.05 ml human plasma; 6 mM disodium EDTA; 2.4 mM phenylmethylsulfonyl fluoride and 1.5 mM 8-hydroxyquinoline (angiotensinase inhibitors); 0.4 mg/ml bovine serum albumin; and 0.024 neomycin sulfate in 100 mM Tris-acetate buffer (pH 7.5). The enzymatic reaction was terminated by boiling the mixture for ten minutes. The quantity of angiotensin I formed was determined by radioimmunoassay, using the general method used in the angiotensin I radioimmunoassay kit of New England Nuclear. Test compounds were considered active if inhibition was greater than 20%.

The following tests illustrate the in vivo antihypertensive activities of the compounds of this invention.

Spontaneously Hypertensive Rat Assay-Indirect Measurement

Male spontaneously hypertensive rats were used in this assay. Initial systolic blood pressure was measured using a caudal plethysmograph immediately before administration of test compounds. For initial screening the test compounds were administered intragastrically at a dose of 50 mg per kg of body weight. Blood pressure readings were obtained at four hours (and in some cases also at 24 hours) after dosing. A compound was rated active if the post-treatment blood pressure was significantly depressed ($P \leq 0.05$) relative to the initial pressure reading.

Spontaneously Hypertensive Rat Assay-Direct Measurement

Male spontaneously hypertensive rats were used in this assay. Using a previously implanted arterial catheter, initial mean arterial blood pressure was measured directly immediately before administration of test compounds. For initial screening the test compounds were administered intragastrically at a dose of 50 mg per kg of body weight. Blood pressure readings were usually obtained at 1, 2, 3, and 4 hours after dosing. A compound was rated active if the mean post-treatment blood pressure was significantly different ($P \leq 0.05$) from that of the concurrent placebo control group.

Renal-ligated Hypertensive Rat Assay

Male Sprague Dawley rats aged 11 to 15 weeks old were used in this test. Three hours after bilateral ligation of the renal arteries, the mean arterial blood pressure (measured directly with previously implanted arterial catheters) and the plasma renin activity increased significantly ($P \leq 0.05$) higher than in sham-operated animals. Test compounds were administered intra-arterially at a dose of 10 mg per kg of body weight, and blood pressure changes were monitored directly at 5, 10, and 15 minutes after injection. A compound was considered active if the post-treatment blood pressure was significantly ($P \leq 0.05$) depressed relative to the placebo control. Under these test conditions pepstatin significantly reduced both mean arterial blood pressure and plasma renin activity.

Rhesus Monkey Blood Pressure Test

Rhesus monkeys were sodium depleted by means of a fruit diet in combination with intramuscular furosemide injections (0.5 mg per kg of body weight) given twice daily for four days. This procedure causes blood pressure to become dependent on plasma renin activity. J. Burton, R. J. Cody, Jr., A. J. Herd, and E. Haber, *Proc. Natl. Acad. Sci. U. S. A.*, 77, 5476-5479 (1980). On the fifth day the animals were anesthetized with ketamine (100 mg administered intravenously). The femoral artery was cannulated for blood pressure measurement and a percutaneous venous cannula was inserted for test compound administration. The animals were allowed to recover from anesthesia and were restrained in a transparent plastic chair. Blood pressure was monitored continuously both before and after test compounds were administered (at 3 mg per kg of body weight). A compound was considered active if post-treatment mean blood pressure was significantly ($P \leq 0.05$) depressed relative to preadministration mean blood pressure. Under these test conditions captopril at 0.1 mg per kg and "renin inhibitory peptide" (RIP, or prolylhistidylprolylphenylalanylhistidylphenylalanyl-phenylalanylvalyltyrosyllysine; see Burton et al., supra) at 1.0 mg per kg significantly lowered mean blood pressure.

Opiate receptor binding of the compounds of this invention illustrated in the examples was tested by the following method. Morphine sulfate is active in this assay.

Opiate Receptor Binding

Membrane homogenates were prepared from whole rat brains (less the cerebellum). A 2 ml portion of the homogenate is incubated at 25° with the test compound (10 mcM) and tritium-labeled naloxone (1.0 nM). After sixty minutes, samples were rapidly cooled on ice, collected over glass-fiber filters, washed with cold buffer, and solubilized by incubation with 1.0 ml of NCS tissue solubilizer. Samples were then prepared for counting in a liquid scintillation counter. Specific binding was calculated, with results expressed as percent inhibition at the test dose. A compound was considered active if inhibition was greater than 50% at 10 mcM. The $IC_{50}$ of each active compound was then determined.

The in vivo analgesic activity of the compounds of this invention illustrated in the examples was tested using the following hot-plate and writhing assays. Tyrosyl-N-(phenylpropyl)-D-alaninamide, a known analog of enkephalin, is active in these assays.

Hot-plate Assay

Male Charles River mice (COBS CD-1(ICR)BR) weighing 20 to 30 grams were used in this assay. Two groups of fourteen mice were placed individually in a restraining cylinder placed on a hot plate kept at 55° ($\pm 0.5°$). The reaction time for each mouse to lick a foot or jump was measured three times at 20 minute intervals. Mice not responding within fifteen seconds were discarded. Twenty minutes after the last reaction experiment ten mice were given a dose of the test compound and ten were given 0.9% saline (each solution containing approximately 0.09 ml of a 1:1 mixture by volume of propylene glycol and polysorbate 80) subcutaneously. The response times of the animals were measured as before at 30, 60, 90, and 120 minute intervals after this injection. Mice not responding within 30 seconds were removed from the hot plate and given a response time of 30 seconds. Analgesia is considered demonstrated in a mouse if the post-drug reaction time is greater than twice the median of the three pre-drug reaction times. A dose of a test compounds was considered active here if 50% of the animals showed analgesia. The $ED_{50}$ of each active test compound was then calculated. See N. B. Eddy, D. Leimbach, *J. Pharmacol. and Exp. Therap.*, 107, 385-393 (1953).

PBQ-Writhing Assay

Male Charles River albino mice (CD-1(ICR)BR) weighing 20 to 30 grams were used in this assay. Thirty minutes after subcutaneous or intragastric administration (0.1 ml per 10 g of body weight) or fifteen minutes after intracerebroventricular administration (5 mcl total volume), a 0.025% solution of phenylbenzoquinone (PBQ) was injected intraperitoneally (0.1 ml per 10 g of body weight). Five minutes later each mouse was placed in a glass beaker and the number of writhes occurring in the next ten minutes was counted. (A writhe consists of dorsoflexion of the back, extension of the hindlimbs, and strong contraction of the abdominal musculature.) The test compound was considered to have produced analgesia in a mouse if the number of writhes elicited by PBQ was equal to or less than one-half the median number of writhes recorded for the saline-treated control group of mice that day. Results were expressed as the number of mice out of a possible ten in which the test compound produced analgesia. If the initial screening dose of 10 mg/kg inhibited writhing in greater than six of ten mice, the effect of additional doses of the compound of the writhing response was evaluated and an $ED_{50}$ was calculated.

By virtue of the antihypertensive activity, the compounds of Formula I are useful in treating high blood pressure in mammals. A physician or veterinarian of ordinary skill can readily determine whether a subject exhibits hypertension. Regardless of the route of administration selected, the compounds of the present invention are formulated into pharmaceutically acceptable dosage forms by conventional methods known to those skilled in the art. The compounds may be formulated using pharmacologically acceptable acid addition salts. Moreover, the compounds or their salts may be used in a suitable hydrated form.

The compounds can be administered in such oral dosage forms as tablets, capsules, pills, powders, or granules. They may also be administered intravascularly, intraperitoneally, subcutaneously, or intramuscularly, using forms known to the pharmaceutical art. In general, the preferred form of administration is oral. An effective but non-toxic quantity of the compound is employed in treatment. The dosage regimen for preventing or treating hypertension with the compounds of this invention is selected in accordance with a variety of factors, including the type, age, weight, sex, and medical condition of the patient; the severity of the hypertension; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention are ordinarily in the range of 1.0 to 20 mg/kg up to about 200 mg/kg orally.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degree celsius unless otherwise noted.

DESCRIPTION OF THE EMBODIMENTS

EXAMPLE 1 t-butoxycarbonyl-N-(2-adamantyl)-L-phenylalaninamide

To a cold (ca −78°) solution of 106 g (0.4 mole) of t-butoxycarbonyl-L-phenylalanine (Boc-Phe) and 88 ml (ca. 0.8 mole) of N-methylmorpholine in 300 ml of dichloromethane, stirred over 30 g of 4A molecular sieves, was added dropwise 52.4 ml (ca. 0.4 mole) of isobutyl chloroformate. The mixture was allowed to warm slowly to 5° and then recooled to about −78°. After adding 75 g (0.4 mole) of 2-aminoadamantane, the mixture was allowed to warm to room temperature and to stir overnight. The mixture was clarified by filtration and washed with several portions of 0.5M sodium bisulfate. The organic layer was heated at reflux over activated charcoal, filtered, dried over sodium sulfate, and concentrated in vacuo to dryness. The resultant title compound was used without further purification in subsequent reactions.

EXAMPLE 2

N-(2-adamantyl)-L-phenylalaninamide hydrochloride

To a stirred solution of 100 g (0.25 mole) of the title product of Example 1 in 827 ml of acetic acid was added 413 ml (2.5 mole) of 6.07N hydrogen chloride in dioxane. After about thirty minutes the solution was concentrated in vacuo to a viscous oil. Trituration with diethyl ether afforded a solid which was collected by filtration, washed with diethyl ether, and air dried. Repetition of the trituration with diethyl ether afforded the title compound as an analytically pure solid. $[\alpha]_D + 47.5°$; $[\alpha]_{365} + 186.3°$ (methanol).

Analysis calcd. for $C_{19}H_{26}N_2O \cdot HCl \cdot \frac{1}{4}H_2O$: C, 67.24; H, 8.17; N, 8.28; Cl, 10.44. Found: C, 67.06; H, 8.16; N, 8.24; Cl, 10.33.

EXAMPLE 3 t-butoxycarbonyl-D-methionylglycine methyl ester

The title compound was prepared by the general method of Example 1 using 198 g (0.79 mole) of t-butoxycarbonyl-D-methionine (Boc-D-Met) and 99.5 g (0.79 mole) glycine methyl ester (Gly-OMe) hydrochloride. The title compound was isolated as an analytically pure solid without further purification.

$[\alpha]_D + 7.9°$; $[\alpha]_{365} + 23.6°$ (methanol).

Analysis calcd. for $C_{13}H_{24}N_2O_5S$: C, 48.73; H, 7.55; N, 8.74; S, 10.01. Found: C, 48.88; H, 7.65; N, 8.53; S, 10.16.

EXAMPLE 4 t-butoxycarbonyl-D-methionylglycine

The title product of Example 3 (100 g, 0.31 mole) was dissolved in 800 ml of tetrahydrofuran to which was then added 42 g (0.62 mole) of potassium hydroxide dissolved in 2 l of water. After hydrolysis was complete—about two hours at room temperature—the mixture was diluted with about 1 l of dichloromethane and acidified (ca. pH 3) with about 1.1 l of 0.5M sodium bisulfate. The aqueous layer was separated and washed with dichloromethane, and all organic layers were recombined. This organic solution was further washed with water, treated with activated carbon, filtered, dried over sodium sulfate, refiltered, and concentrated in vacuo to an oil. Trituration with diethyl ether afforded a solid which was collected by filtration, washed with diethyl ether, and dried, giving 73 g of analytically pure title compound, m.p. 124.5°–125.5°.

Analysis calcd. for $C_{12}H_{22}N_2O_5S$: C, 47.04; H, 7.24; N, 9.14; S, 10.46. Found: C, 47.08; H, 7.22; N, 9.06; S, 10.50.

Concentration of the filtrate, followed by trituration with diethyl ether and column chromatography on silica gel, afforded 5.7 g of additional title compound.

EXAMPLE 5 t-butoxycarbonyl-D-methionylglycyl-N-(2-adamantyl)-L-phenylalaninamide hemihydrate The title compound was prepared by the general method of Example 1 using the title products of Example 2 (37.3 g, 0.11 mole) and Example 4 (35.0 g, 0.11 mole) in 250 ml of dichloromethane. The title compound was obtained as an analytically pure solid, m.p. 97°–102°.

$[\alpha]_D -14.1°$; $[\alpha]_{365} -46.9°$ (chloroform).

Analysis calcd. for $C_{31}H_{46}N_4O_5S \cdot \frac{1}{2}H_2O$: C, 62.49; H, 7.95; N, 9.40; S, 5.38. Found: C, 62.78; H, 7.91; N, 9.36; S, 5.60.

EXAMPLE 6

D-methionylglycyl-N-(2-adamantyl)-L-phenylalaninamide hydrochloride hydrate

The title compound (17.4 g) was prepared by the method of Example 2 using 20.0 g (0.034 mole) of the title product of Example 5.

Analysis calcd. for $C_{26}H_{38}N_4O_3S \cdot HCl \cdot H_2O$: C, 57.70; H, 7.63; N, 10.35; S, 5.92. Found: C, 57.16; H, 7.55; N, 10.19; S, 6.01.

EXAMPLE 7 t-butoxycarbonyl-L-phenylalanyl-D-methionylglycyl-N-(2-adamantyl)-L-phenylalaninamide The title compound was prepared by the general method of Example 1 using t-butoxycarbonyl-L-phenylalanine (2.3 g, 8.6 mmole) and the title product of Example 6 (4.5 g, 8.6 mmole) in 50 ml of dichloromethane stirred with 5A molecular sieves. The crude product was purified by column chromatography on silica gel, giving 4.7 g of analytically pure title compound.

$[\alpha]_D -2.9$; $[\alpha]_{365} -6.3°$ (chloroform).

Analysis calcd. for $C_{40}H_{55}N_5O_6S$: C, 65.45; H, 7.55; N, 9.54; S, 4.37. Found: C, 65.14; H, 7.53; N, 9.48; S, 4.63.

EXAMPLE 8

L-phenylalanyl-D-methionylglycyl-N-(2-adamantyl)-L-phenylalaninamide hydrochloride

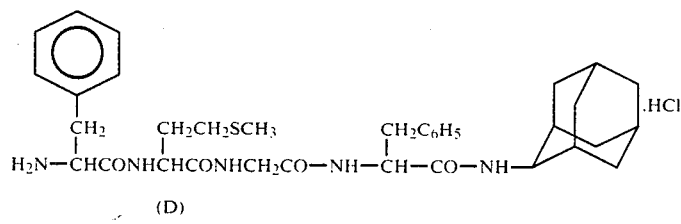

(D)

The title compound (2.4 g) was prepared by the method of Example 2 using 4.7 g (6.4 mmole) of the title product of Example 7.

$[\alpha]_D +26.5°$; $[\alpha]_{365} +99.0°$ (methanol).

Analysis calcd. for $C_{35}H_{47}N_5O_4S \cdot HCl$: C, 62.71; H, 7.22; N, 10.45; S, 4.78; Cl, 5.29. Found: C, 62.41; H, 7.17; N, 10.25; S, 4.82; Cl, 5.20.

EXAMPLE 9 t-butoxycarbonyl-$N^\alpha$-methyl-L-phenylalanyl-D-methionylglycyl-N-(2-adamantyl)-L-phenylalaninamide The title compound (2.4 g) was prepared by the general method described in Example 7 using t-butoxycarbonyl-N-methylphenylalanine in place of t-butoxycarbonyl-L-phenylalanine.

$[\alpha]_D -59.2°$; $[\alpha]_{365} -225.5°$ (chloroform).

Analysis calcd. for $C_{41}H_{57}N_5O_6S$: C, 65.83; H, 7.68; N, 9.36; S, 4.29. Found: C, 65.96; H, 7.72; N, 9.33; S, 4.31.

EXAMPLE 10

$N^\alpha$-methyl-L-phenylalanyl-D-methionylglycyl-N-(2-adamantyl)-L-phenylalaninamide hydrochloride

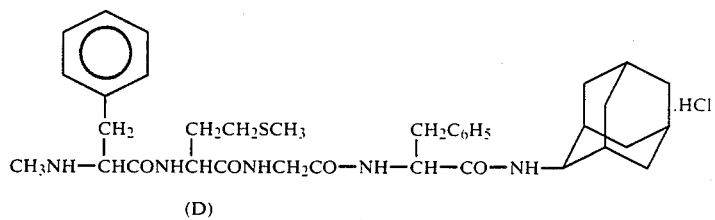

(D)

The title compound (2.1 g) was prepared by the method of Example 8 using the title product of Example 9.

$[\alpha]_D +31.6°$; $[\alpha]_{365} +110.7°$ (methanol).

Analysis calcd. for $C_{36}H_{49}N_5O_4S \cdot HCl$: C, 63.18; H, 7.36; N, 10.23; S, 4.68; Cl, 5.18. Found: C, 62.95; H, 7.36; N, 10.13; S, 4.65; Cl, 5.15.

EXAMPLE 11 t-butoxycarbonyl-N-ethylphenylalanine ethyl ester

To a mixture of 2.65 g (10 mmole) of Boc-Phe in 50 ml of cold (ca. −78°), dry tetrahydrofuran was added 12 ml (ca. 22 mmole) of 1.9M t-butyllithium. After thirty minutes, the mixture was allowed to warm to −20° and then to react with 4.2 g (22 mmole) of triethyloxonium fluoborate. After thirty minutes, the mixture was allowed to warm to 0° and then poured into water and extracted with dichloromethane. The organic extract was washed sequentially with portions of 5% aqueous sodium bicarbonate and water, dried over sodium sulfate, filtered, and concentrated to dryness. Distillation (ca. 130°–200°) afforded an oil that was further purified by column chromatography on silica gel to give the title compound (4.7 g) as an analytically pure solid, m.p. 58°–61.5°.

[α]$_D$ −131.5°; [α]$_{365}$ −472.5° (methanol).

Analysis calcd. for C$_{18}$H$_{27}$NO$_4$: C, 67.26; H, 8.47; N, 4.36. Found: C, 67.54; H, 8.59; N, 4.57.

EXAMPLE 12 t-butoxycarbonyl-N-ethylphenylalanine, Method A

To a stirred mixture of 16 g (0.05 mole) of t-butoxycarbonyl-N-ethylphenylalanine ethyl ester (prepared as in Example 11) in 200 ml of tetrahydrofuran was added 6.6 g (0.1 mole) of potassium hydroxide in 400 ml of water. After the mixture was stirred overnight, 400 ml of dichloromethane was added and the mixture acidified to pH 3 with 0.5M sodium bisulfate. The aqueous layer was separated and washed with dichloromethane, and all organic layers were recombined. This organic solution was further washed with water, dried over sodium sulfate, filtered, and concentrated in vacuo to dryness. Column chromatography on silica gel afforded 10.9 g of the analytically pure title compound.

[α]$_D$ −158.4°; [α]$_{365}$ −555.0° (methanol).
[α]$_D$ −120.2°; [α]$_{365}$ −437.4° (chloroform).

Analysis calcd. for C$_{16}$H$_{23}$NO$_4$: C, 65.51; H, 7.90; N, 4.77. Found: C, 65.51; H, 8.11; N, 4.82.

EXAMPLE 13 t-butoxycarbonyl-N-ethylphenylalanine, Method B

The title compound was prepared by the general method of Example 11, except that only one equivalent of triethyloxonium fluoborate was used. After reaction was complete, the mixture was poured into water and washed with dichloromethane. The basic aqueous layer was acidified (pH 5) with 0.5M sodium bisulfate and extracted with dichloromethane. The organic layer was dried over sodium sulfate, filtered, concentrated to dryness, and purified by column chromatography. The product prepared by this method was the same as that prepared by the methods of Examples 11 and 12.

EXAMPLE 14 t-butoxycarbonyl-N$^α$-ethyl-L-phenylalanyl-D-methionylglycyl-N-(2-adamantyl)-L-phenylalaninamide The title compound (3.0 g), m.p. 175°–178.5°, was prepared by the general method described in Example 7 using t-butoxycarbonyl-N-ethylphenylalanine (See Example 12 or 13) in place of t-butoxycarbonyl-L-phenylalanine. [α]$_D$ −68.3°; [α]$_{365}$ −268.7° (chloroform)

Analysis calcd. for C$_{42}$H$_{59}$N$_5$O$_6$S: C, 66.20; H, 7.80; N, 9.19; S, 4.21. Found: C, 66.18; H, 7.84; N, 9.12; S, 4.28.

EXAMPLE 15

N$^α$-ethyl-L-phenylalanyl-D-methionylglycyl-N-(2-adamantyl)-L-phenylalaninamide hydrochloride

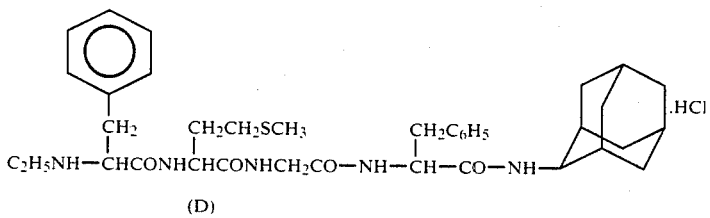

(D)

The title compound (3.5 g) was prepared by the method of Example 8 using the title product of Example 14.

Analysis called for C$_{37}$H$_{51}$N$_5$O$_4$S.HCl: C, 63.63; H, 7.51; N, 10.03; S, 4.59; Cl, 5.08. Found: C, 63.34; H, 7.55; N, 10.00; S, 4.56; Cl, 5.12.

EXAMPLE 16

L-phenylalanyl-[4-(methylsulfinyl)-D-2-aminobutanoyl]glycyl-N-(2-adamantyl)-L-phenylalaninamide hydrochloride hemihydrate

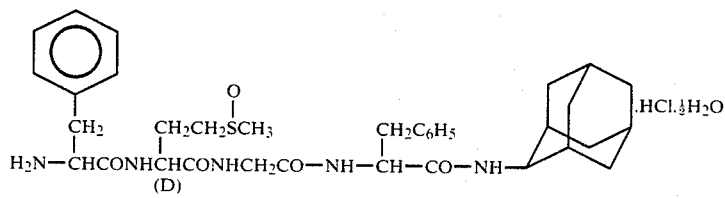

(D)

To a solution of the title product of Example 8 (2.0 g) in 75 ml of methanol was added 20 ml of 30% aqueous hydrogen peroxide. After one hour at room temperature, the reaction mixture was concentrated in vacuo to a glassy solid. Trituration with diethyl ether afforded 1.93 g of the title compound as a white solid.

[α]$_D$ +26.5°; [α]$_{365}$ +93.1° (methanol).

Analysis calcd. for C$_{35}$H$_{47}$N$_5$O$_5$S.HCl.½H$_2$O: C, 60.46; H, 7.10; N, 10.07; S, 4.61; Cl, 5.10. Found: C, 60.11; H, 6.99; N, 10.00; S, 4.709; Cl, 5.10.

EXAMPLE 17

N$^α$-methyl-L-phenylalanyl-[4-(methylsulfinyl)-D-2-aminobutanoyl]glycyl-N-(2-adamantyl)-L-phenylalaninamide hydrochloride

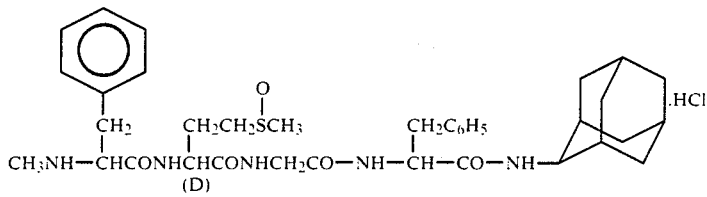

The title compound (1.2 g) was prepared by the method of Example 16 using the title product of Example 10.

[α]$_D$ +28.7°; [α]$_{365}$ +109.6° (methanol).

Analysis calcd. for C$_{36}$H$_{49}$N$_5$O$_5$S.HCl: C, 61.74; H, 7.20; N, 10.00; S, 4.58; Cl, 5.06. Found: C, 61.31; H, 7.12; N, 9.96; S, 4.58; Cl, 5.19.

EXAMPLE 18

N$^α$-ethyl-L-phenylalanyl-[4-(methylsulfinyl)-D-2-aminobutanoly]glycyl-N-(2-adamantyl)-L-phenylalaninamide hydrochloride hemihydrate

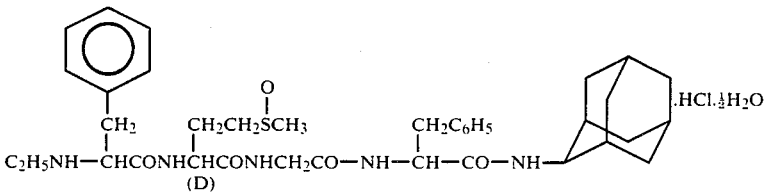

The title compound (92 mg) was prepared by the method of Example 16 using the title product of Example 15.

[α]$_D$ +31.6°; [α]$_{365}$ +110.7° (methanol).

Analysis calcd. for C$_{37}$H$_{51}$N$_5$O$_5$S.HCl.½H$_2$O: C, 61.43; H, 7.38; N, 9.68; S, 4.43; Cl, 4.91. Found: C, 61.35; H, 7.28; N, 9.55; S, 4.52; Cl, 4.97.

EXAMPLE 19

4-t-butyl-D,L-phenylalanine

To a solution of sodium ethoxide in ethanol, formed by the heating 27.7 g (1.21 mole) of sodium metal with 1 liter of absolute ethanol, was added 222.5 g (1.08 mole) of diethyl formamidomalonate. After the malonate anion had formed, 4-t-butylbenzyl chloride was added and the mixture was heated for about four hours at reflux. Excess sodium ethoxide was destroyed by adding acetic acid, and the reaction mixture was concentrated in vacuo to dryness. The residue was triturated and concentrated in vacuo, successively using dichloromethane and diethyl ether.

Without further purification, the oily benzylated malonate intermediate (263 g) was dissolved in about 1000 ml of methanol containing 500 ml of concentrated hydrochloric acid and heated at reflux for six hours. Upon cooling, the reaction mixture produced a crystalline precipitate that was collected and washed with diethyl ether, giving 188 g of the title product as the hydrochloride salt.

Analysis calcd. for C$_{13}$H$_{19}$NO$_2$.HCl: C, 60.58; H, 7.82; N, 5.43; Cl, 13.75. Found: C, 60.76; H, 7.98; N, 5.39; Cl, 13.48.

Concentration of the filtrate from which the title compound was crystallized produced a quantity of crystals comprised essentially of the methyl ester of the title compound. Hydrolysis in 10% aqueous sodium carbonate warmed on a steam bath afforded an additional 3.5 g of the title compound as the free base.

EXAMPLE 20 t-butoxycarbonyl-4-t-butyl-D,L-phenylalanine

The title compound of Example 19 (3.4 g, 15.4 mmole) was dissolved in a mixture of 30 ml of dioxane and 30 ml of water adjusted to pH 10.5 with 4N sodium hydroxide. Di-t-butyl dicarbonate (3.7 g, 17 mmole) was added and the solution was maintained at pH 10.5 by automatic titration with 2N sodium hydroxide. After about one hour the mixture was concentrated in vacuo and the residue redissolved in water. The resultant solution was washed with diethyl ether, adjusted to pH 2 with 1M potassium bisulfate, and extracted with ethyl acetate. The organic phase was washed with saturated aqueous sodium chloride, dried over sodium sulfate, filtered, and concentrated to dryness. Recrystallization from cold (ca. −78°) pentane afforded 3.7 g of the title product.

Analysis calcd. for C$_{18}$H$_{27}$NO$_4$: C, 67.26; H, 8.47; N, 4.36. Found: C, 67.38; H, 8.75; N, 4.19.

EXAMPLE 21 t-butoxycarbonyl-4-t-butyl-D,L-phenylalanyl-D-methionylglycyl-N-(2-adamantyl)-L-phenylalaninamide hemihydrate The title compound (5.0 g) was prepared by the general method described in Example 7 using the title product of Example 20 in place of t-butoxycarbonyl-L-phenylalanine.

[α]$_D$ −1.6°; [α]$_{365}$ −4.8° (chloroform).

Analysis calcd. for C$_{44}$H$_{63}$N$_5$O$_6$S.½H$_2$O: C, 66.13; H, 8.07; N, 8.77; S, 4.01. Found: C, 66.11; H, 7.95; N, 8.73; S, 4.19.

EXAMPLE 22

4-t-butyl-D,L-phenylalanyl-D-methionylglycyl-N-(2-adamantyl)-L-phenylalaninamide hydrochloride hemihydrate

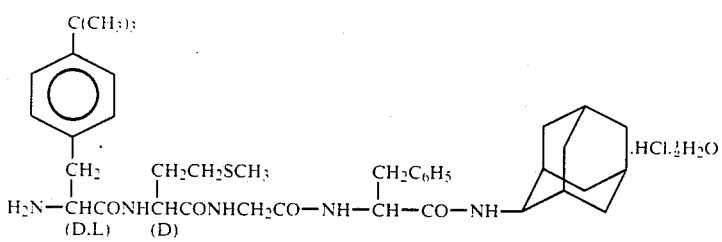

The title compound (4.2 g) was prepared by the method of Example 8 using the title product of Example 21.

[α]$_D$ +9.9°; [α]$_{365}$ +26.9° (methanol).

Analysis calcd. for C$_{39}$H$_{55}$N$_5$O$_4$S.HCl.½H$_2$O: C, 63.69; H, 7.81; N, 9.52; S, 4.36; Cl, 4.82. Found: C, 63.31; H, 7.63; N, 9.52; S, 4.32; Cl, 4.86

EXAMPLE 23

4-t-butyl-D,L-phenylalanyl-[4-(methylsulfinyl)-D-2-aminobutanoyl]glycyl-N-(2-adamantyl)-L-phenylalaninamide hydrochloride hemihydrate

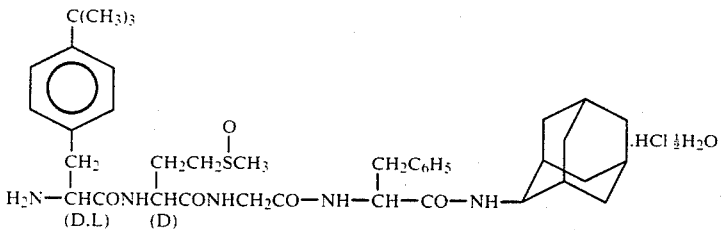

The title compound (970 mg) was prepared by the method of Example 16 using the title product of Example 22.

[α]$_D$ +11.8°; [α]$_{365}$ +36.4° (methanol).

Analysis calcd. for C$_{39}$H$_{55}$N$_5$O$_5$S.HCl.½H$_2$O: C, 62.33; H, 7.64; N, 9.32; S, 4.27; Cl, 4.72. Found: C, 62.43; H, 7.65; N, 9.30; S, 4.34; Cl, 4.62.

EXAMPLES 24–30

The following compounds, Examples 24–30, were prepared from the title product of Example 6 using the following general methods. Using the method described in Example 1 or the modified method described in Example 7, intermediate t-butoxycarbonyl-protected derivatives of the title compounds were prepared by substituting appropriate t-butoxycarbonyl-protected amino acids for t-butoxycarbonyl-D-phenylalanine. The t-butoxycarbonyl-protected amino acids are commercially available or are readily prepared by methods known in the art (e.g., Example 20) from the corresponding unprotected amino acids. The title compounds are prepared as hydrochloride salts from the protected intermediates by the method described in Example 2.

EXAMPLE 24

D-phenylalanyl-D-methionylglycyl-N-(2-adamantyl)-L-phenylalaninamide hydrochloride t-butoxycarbonyl intermediate: [α]$_D$ +6.0°; [α]$_{365}$ +16.6° (chloroform).

Analysis calcd. for C$_{40}$H$_{55}$N$_5$O$_6$S: C, 65.45; H, 7.55; N, 9.54; S, 4.37. Found: C, 65.47; H, 7.63; N, 9.48; S, 4.63.

Title compound: [α]$_D$ −14.5°; [α]$_{365}$ −65.5° (methanol).

Analysis calcd. for C$_{35}$H$_{47}$N$_5$O$_4$S.HCl: C, 62.71; H, 7.22; N, 10.45; S, 4.78; Cl, 5.29. Found: C, 62.36; H, 7.24; N, 10.27; S, 4.73; Cl, 4.77.

EXAMPLE 25

4-fluoro-D,L-phenylalanyl-D-methionylglycyl-N-(2-adamantyl)-L-phenylalaninamide hydrochloride ¼ hydrate

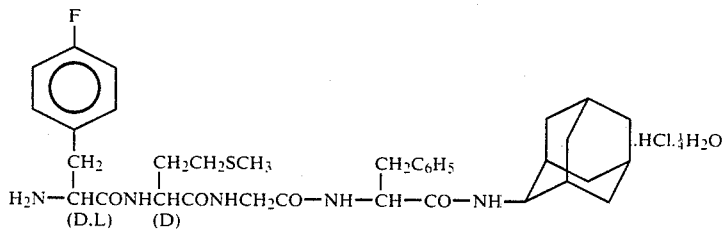

t-butoxycarbonyl intermediate: [α]$_D$ −3.4°; [α]$_{365}$ −16.6° (chloroform).

Analysis calcd. for C$_{40}$H$_{54}$N$_5$O$_6$SF: C, 63.89; H, 7.23; N, 9.31; S, 4.26; F, 2.53. Found: C, 63.84; H, 7.33; N, 9.24; S, 4.31; F, 2.46.

Title compound: [α]$_D$ +10.7°; [α]$_{365}$ +32° (methanol).

Analysis calcd. for C$_{35}$H$_{46}$N$_5$O$_4$SF.HCl.¼H$_2$O: C, 60.68; H, 6.91; N, 10.11; S, 4.63; Cl, 5.12. Found: C, 60.51; H, 6.87; N, 10.08; S, 4.63; Cl, 5.21.

EXAMPLE 26

L-phenylglycyl-D-methionylglycyl-N-(2-adamantyl)-L-phenylalaninamide hydrochloride hemihydrate

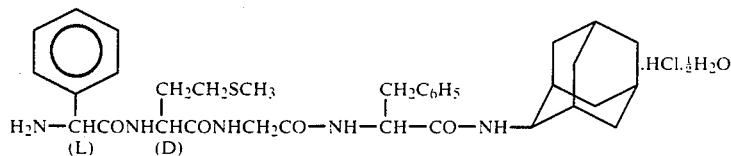

t-butoxycarbonyl intermediate: not analytically pure.
Title compound: Analysis calcd. for C$_{34}$H$_{45}$N$_5$O$_4$S.HCl.½H$_2$O: C, 61.38; H, 7.12; N, 10.53; S, 4.82. Found: C, 61.21; H, 7.05; N, 10.41; S, 4.71.

EXAMPLE 27

D-phenylglycyl-D-methionylglycyl-N-(2-adamantyl)-L-phenylalaninamide hydrochloride hemihydrate t-butoxycarbonyl intermediate: not analytically pure.
Title compound: Analysis calcd. for C$_{34}$H$_{45}$N$_5$O$_4$S.HCl.H$_2$O: C, 60.56; H, 7.17; N, 10.39; S, 4.75. Found: C, 60.74; H, 6.90; N, 10.42; S, 4.89.

EXAMPLE 28

L-2-amino-4-phenylbutanoyl-D-methionylglycyl-N-(2-adamantyl)-L-phenylalaninamide hydrochloride

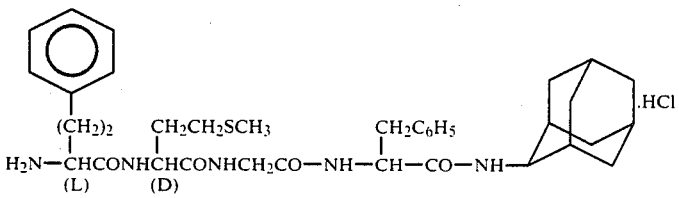

t-butoxycarbonyl intermediate: not analytically pure.
Title compound: [α]$_D$ +11.7° (methanol).
Analysis calcd. for C$_{36}$H$_{49}$N$_5$O$_4$S.HCl: C, 63.18; H, 7.36; N, 10.23; S, 4.68. Found: C, 63.15; H, 7.35; N, 10.12; S, 4.65.

EXAMPLE 29

3-(2-naphthalenyl)-L-alanyl-D-methionylglycyl-N-(2-adamantyl)-L-phenylalaninamide hydrochloride

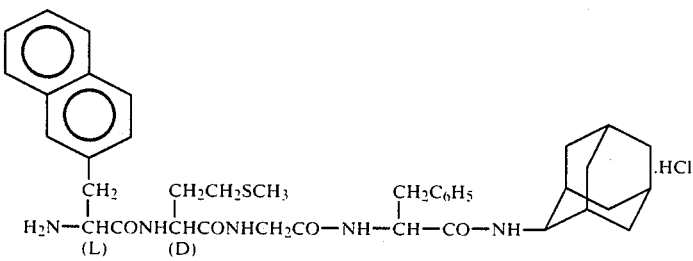

t-butoxycarbonyl intermediate: [α]$_D$ −12.8°; [α]$_{365}$ −27.2° (chloroform).
Analysis calcd. for C$_{44}$H$_{57}$N$_5$O$_6$S: C, 67.40; H, 7.33; N, 8.93; S, 4.09. Found: C, 66.92; H, 7.33; N, 8.84; S, 4.05.
Title compound: [α]$_D$ +27.3°; [α]$_{365}$ +91.8° (methanol).
Analysis calcd. for C$_{39}$H$_{49}$N$_5$O$_4$S.HCl: C, 65.02; H, 7.00; N, 9.72; S, 4.45; Cl, 4.92. Found: C, 64.81; H, 7.09; N, 9.68; S, 4.51; Cl, 5.10.

EXAMPLE 30

L-tryptophanyl-D-methionylglycyl-N-(2-adamantyl)-L-phenylalaninamide hydrochloride t-butoxycarbonyl intermediate: [α]$_D$ +9.2°; [α]$_{365}$ +36.4° (chloroform).
Analysis calcd. for C$_{42}$H$_{56}$N$_6$O$_6$S: C, 65.26; H, 7.30; N, 10.87; S, 4.15. Found: C, 65.68; H, 7.40; N, 10.34; S, 4.04.
Title compound: [α]$_D$ +17.5°; [α]$_{365}$ +84.8° (methanol).
Analysis calcd. for C$_{37}$H$_{48}$N$_6$O$_4$S.HCl: C, 62.65; H, 6.96; N, 11.85; S, 4.52; Cl, 5.00. Found: C, 62.21; H, 7.04; N, 11.66; S, 4.58; Cl, 4.93.

EXAMPLE 31

D-methionylglycyl-N-(1-adamantyl)-L-phenylalaninamide hydrochloride

The title compound was prepared by the methods of Examples 1, 2, 5, and 6 using 1-aminoadamantane instead of 2-aminoadamantane.

[α]$_D$ −17.4°; [α]$_{365}$ −53.0° (methanol).
Analysis calcd. for C$_{26}$H$_{38}$N$_4$O$_3$.HCl: C, 59.69; H, 7.51; N, 10.71; S, 6.13; Cl, 6.78. Found: C, 59.36; H, 7.44; N, 10.62; S, 6.18; Cl, 6.80.

EXAMPLE 32 t-butoxycarbonyl-N$^α$-ethyl-L-phenylalanyl-D-methionylglycyl-N-(1-adamantyl)-L-phenylalaninamide The title compound (1.6 g) was prepared by the general method described in Example 14 using the 1-adamantyl title product of Example 31.

[α]$_D$ −57.4°; [α]$_{365}$ −230.4° (chloroform).
Analysis calcd. for C$_{42}$H$_{59}$N$_5$O$_6$S: C, 66.20; H, 7.80; N, 9.19; S, 4.21. Found: C, 66.45; H, 7.86; N, 9.02; S, 4.20.

EXAMPLE 33

N$^\alpha$-ethyl-L-phenylalanyl-D-methionylglycyl-N-(1-adamantyl)-L-phenylalaninamide hydrochloride hemihydrate

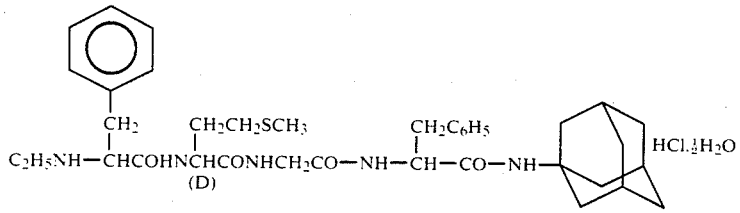

The title compound (1.3 g) was prepared by the method summarized in Example 8 using the title product of Example 32.

[α]$_D$ +37.6°; [α]$_{365}$ +136.8° (methanol).

Analysis calcd. for C$_{37}$H$_{51}$N$_5$O$_4$S.HCl.½H$_2$O: C, 62.82; H, 7.55; N, 9.90; S, 4.53; Cl, 5.01. Found: C, 62.85; H, 7.44; N, 9.76; S, 4.45; Cl, 5.31.

EXAMPLE 34

D-methionylglycyl-N-(2-adamantyl)-D-phenylalaninamide hydrochloride hemihydrate

The title compound was prepared by the methods of Examples 1, 2, 5, and 6 using t-butoxycarbonyl-D-phenylalanine instead of t-butoxycarbonyl-L-phenylalanine.

[α]$_D$ +11.4°; [α]$_{365}$ +77.6° (methanol).

Analysis calcd. for C$_{26}$H$_{38}$N$_4$O$_3$S.HCl.½H$_2$O: C, 58.68; H, 7.57; N, 10.53; S, 6.02; Cl, 6.66. Found: C, 58.56; H, 7.52; N, 10.49; S, 6.22; Cl, 6.92.

EXAMPLE 35 t-butoxycarbonyl-N$^\alpha$-ethyl-L-phenylalanyl-D-methionylglycyl-N-(2-adamantyl)-D-phenylalaninamide The title compound (2.0 g) was prepared by the general method described in Example 14 using the title product of Example 34.

[α]$_D$ −49.0°; [α]$_{365}$ −185.6° (chloroform).

Analysis calcd. for C$_{42}$H$_{59}$N$_5$O$_6$S: C, 66.20; H, 7.80; N, 9.19; S, 4.21. Found: C, 65.81; H, 7.85; N, 9.38; S, 4.24.

EXAMPLE 36

N$^\alpha$-ethyl-L-phenylalanyl-D-methionylglycyl-N-(2-adamantyl)-D-phenylalaninamide hydrochloride hemihydrate The title compound (1.9 g) was prepared by the method summarized in Example 8 using the title product of Example 35.

[α]$_D$ +58.3°; [α]$_{365}$ +207.4° (methanol).

Analysis calcd. for C$_{37}$H$_{51}$N$_5$O$_4$S.HCl.½H$_2$O: C, 62.82; H, 7.55; N, 9.90. Found: C, 62.60; H, 7.47; N, 9.88.

EXAMPLE 37

D-methionylglycyl-N-(2-adamantyl)-N$^\alpha$-methyl-L-phenylalaninamide hydrochloride hemihydrate The title compound was prepared by the methods of Examples 1, 2, 5, and 6 using t-butoxycarbonyl-N-methyl-L-phenylalanine instead of t-butoxycarbonyl-L-phenylalanine.

[α]$_D$ −44.9°; [α]$_{365}$ −171.7° (methanol).

Analysis calcd. for C$_{27}$H$_{40}$N$_4$O$_3$S.HCl.½H$_2$O: C, 59.37; H, 7.75; N, 10.26; S, 5.87; Cl, 6.49. Found: C, 59.65; H, 7.60; N, 10.26; S, 5.77; Cl, 6.78.

EXAMPLE 38 t-butoxycarbonyl-N$^\alpha$-ethyl-L-phenylalanyl-D-methionylglycyl-N-(2-adamantyl)-N$^\alpha$-methyl-L-phenylalaninamide The title compound (2.6 g) was prepared by the general method described in Example 14 using the title product of Example 37.

[α]$_D$ −67.2°; [α]$_{365}$ −280.8° (chloroform).

Analysis calcd. for C$_{43}$H$_{61}$N$_5$O$_6$S: C, 66.55; H, 7.72; N, 9.03; S, 4.13. Found: C, 66.50; H, 7.99; N, 8.73; S, 4.00.

EXAMPLE 39

N$^\alpha$-ethyl-L-phenylalanyl-D-methionylglycyl-N-(2-adamantyl)-N$^\alpha$-methyl-L-phenylalaninamide hydrochloride hemihydrate

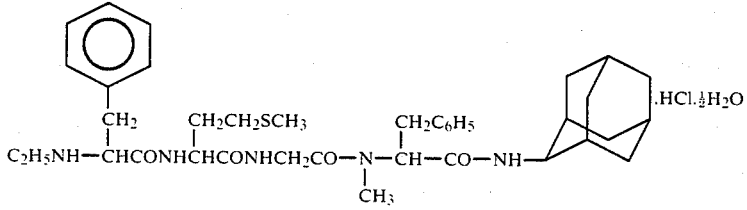

The title compound (1.4 g) was prepared by the method summarized in Example 8 using the title product of Example 38.

[α]$_D$ +22.7°; [α]$_{365}$ +75.8° (methanol).

Analysis calcd. for C$_{38}$H$_{53}$N$_5$O$_4$S.HCl.½H$_2$O: C, 63.27; H, 7.68; N, 9.71; S, 4.44; Cl, 4.91. Found: C, 63.34; H, 7.66; N, 9.70; S, 4.46; Cl, 4.96.

EXAMPLES 40–44

The following "methionine sulfoxide" compounds, Examples 40–44, were prepared from the corresponding methionine-containing compounds described above using the general method described in Example 16.

EXAMPLE 40

4-fluoro-D,L-phenylalanyl-[(4-(methylsulfinyl)-D-2-aminobutanoyl]glycyl-N-(2-adamantyl)-L-phenylalaninamide hydrochloride hemihydrate $[\alpha]_D$ +8.4°; $[\alpha]_{365}$ +34.4° (methanol).

Analysis calcd. for $C_{35}H_{46}N_5O_5SF.HCl.\frac{1}{4}H_2O$: C, 58.93; H, 6.78; N, 9.82; S, 4.49; Cl, 4.97. Found: C, 59.09; H, 6.60; N, 9.80; S, 4.61; Cl, 4.97.

EXAMPLE 41

L-phenylglycyl-[4-(methylsulfinyl)-D-2-aminobutanoyl]glycyl-N-(2-adamantyl)-L-phenylalaninamide hydrochloride hydrate Analysis calcd. for $C_{34}H_{45}N_5O_5S.HCl.H_2O$: C, 59.16; H, 7.01; N, 10.15; S, 4.64. Found: C, 59.16; H, 6.96; N, 10.12; S, 4.66.

EXAMPLE 42

L-2-amino-4-phenylbutanoyl-[4-(methylsulfinyl)-D-2-aminobutanoyl]-glycyl-N-(2-adamantyl)-L-phenylalaninamide hydrochloride hemihydrate Analysis calcd. for $C_{36}H_{49}N_5O_5S.HCl.\frac{1}{2}H_2O$: C, 60.96; H, 7.25; N, 9.87; S, 4.52. Found: C, 61.02; H, 7.01; N, 9.76; S, 4.61.

EXAMPLE 43

3-(2-naphthalenyl)-L-alanyl-[4-(methylsulfinyl)-D-2-aminobutanoyl]glycyl-N-(2-adamantyl)-L-phenylalaninamide hydrochloride $[\alpha]_D$ +16.9°; $[\alpha]_{365}$ +64° (methanol).

Analysis calcd. for $C_{39}H_{49}N_5O_5S.HCl.\frac{1}{2}H_2O$: C, 62.84; H, 6.90; N, 9.40; S, 4.30; Cl, 4.76. Found: C, 62.61; H, 6.84; N, 9.21; S, 4.34; Cl, 4.79.

EXAMPLE 44

$N^\alpha$-ethyl-L-phenylalanyl-[4-(methylsulfinyl)-D-2-aminobutanoyl]glycyl-N-(2-adamantyl)-$N^\alpha$-methyl-L-phenylalaninamide hydrochloride sesquihydrate $[\alpha]_D$ +32°; $[\alpha]_{365}$ +87.7° (methanol). Analysis calcd. for $C_{38}H_{53}N_5O_5S.HCl.3/2H_2O$: C, 60.41; H, 7.60; N, 9.27. Found: C, 60.67; H, 7.33; N, 9.38.

EXAMPLE 45

$N^\alpha$-ethyl-L-phenylalanyl-D-methionylglycyl-N-(2-adamantyl)-L-phenylalaninamide The title product of Example 15 is stirred under argon in water contining a molar excess of potassium bicarbonate. After about one hour the mixture is extracted with dichloromethane, and the organic layer is dried over sodium sulfate, filtered, and concentrated in vacuo to produce the title compound as the free base.

What is claimed is:

1. A compound of the formula:

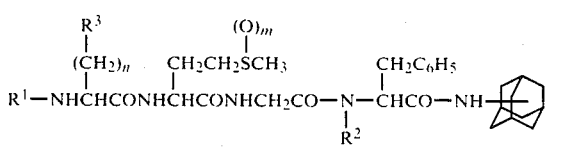

wherein $R^1$ is:
(a) hydrogen; or
(b) alkyl of 1 to 6 carbon atoms, inclusive;
wherein $R^2$ is:
(a) hydrogen; or
(b) alkyl of 1 to 6 carbon atoms, inclusive;

wherein $R^3$ is:

(a) 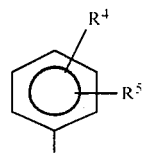

(b) 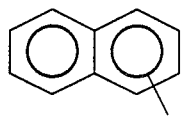

(c) 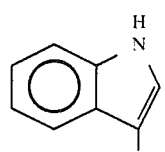

wherein $R^4$ and $R^5$, each being the same or different, are:
(a) hydrogen;
(b) alkyl of 1 to 6 carbon atoms, inclusive; or
(c) halogen;
wherein m is 0, 1, or 2;
wherein n is 0 or an integer of from 1 to 4; and the stereochemical configuration of each of the optically active amino acid residues may independently be D, l, or DL; and the pharmaceutically acceptable salts thereof.

2. A compound according to claim 1 having the formula:

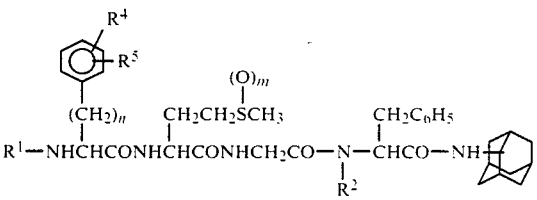

and the stereochemical configuration of each of the optically active amino acid residues may independently be D, L, or DL; and the pharmaceutically acceptable salts thereof.

3. A compound according to claim 2 having the formula:

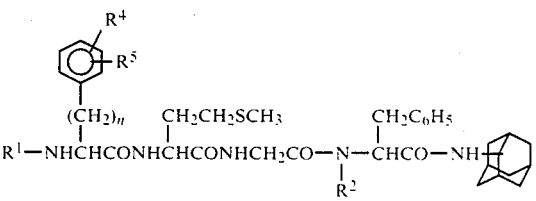

and the stereochemical configuration of each of the optically active amino acid residues may independently be D, L, or DL; and the pharmaceutically acceptable salts thereof.

4. A compound according to claim 3 wherein n is 0.

5. A compound according to claim 4, which is L-phenylglycyl-D-methionylglycyl-N-(2-adamantyl)-L-phenylalaninamide.

6. A compound according to claim 4, which is D-phenylglycyl-D-methionylglycyl-N-(2-adamantyl)-L-phenylalaninamide.

7. A compound according to claim 3 wherein n is 1.

8. A compound according to claim 7 having the formula:

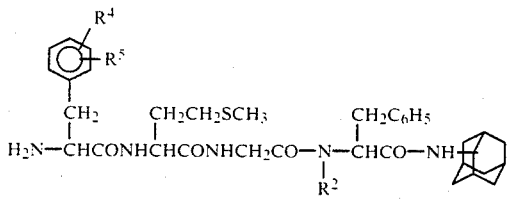

and the stereochemical configuration of each of the optically active amino acid residues may independently be D, L, or DL; and the pharmaceutically acceptable salts thereof.

9. A compound according to claim 8, which is L-phenylalanyl-D-methionylglycyl-N-(2-adamantyl)-L-phenylalaninamide.

10. A compound according to claim 8, which is D-phenylalanyl-D-methionylglycyl-N-(2-adamantyl)-L-phenylalaninamide.

11. A compound according to claim 8, which is 4-t-butyl-D,L-phenylalanyl-D-methionylglycyl-N-(2-adamantyl)-L-phenylalaninamide.

12. A compound according to claim 8, which is 4-fluoro-D,L-phenylalanyl-D-methionylglycyl-N-(2-adamantyl)-L-phenylalaninamide.

13. A compound according to claim 7 having the formula:

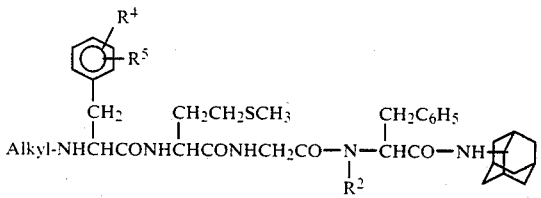

and the stereochemical configuration of each of the optically active amino acid residues may independently be D, L, or DL; and the pharmaceutically acceptable salts thereof.

14. A compound according to claim 13, which is $N^\alpha$-methyl-L-phenylalanyl-D-methionylglycyl-N-(2-adamantyl)-L-phenylalaninamide.

15. A compound according to claim 13, which is $N^\alpha$-ethyl-L-phenylalanyl-D-methionylglycyl-N-(2-adamantyl)-L-phenylalaninamide.

16. A compound according to claim 13, which is $N^\alpha$-ethyl-L-phenylalanyl-D-methionylglycyl-N-(2-adamantyl)-D-phenylalaninamide.

17. A compound according to claim 13, which is $N^\alpha$-ethyl-L-phenylalanyl-D-methionylglycyl-N-(1-adamantyl)-L-phenylalaninamide.

18. A compound according to claim 13, which is $N^\alpha$-ethyl-L-phenylalanyl-D-methionylglycyl-N-(2-adamantyl)-$N^\alpha$-methyl-L-phenylalaninamide.

19. A compound according to claim 3 wherein n is 2.

20. A compound according to claim 19, which is L-2-amino-4-phenylbutanoyl-D-methionylglycyl-N-(2-adamantyl)-L-phenylalaninamide.

21. A compound according to claim 2 having the formula:

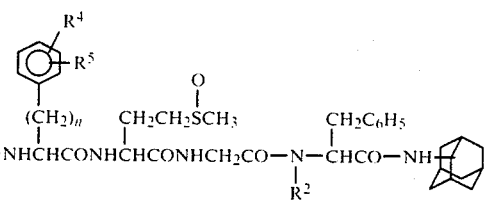

and the stereochemical configuration of each of the optically active amino acid residues may independently be D, L, or DL; and the pharmaceutically acceptable salts thereof.

22. A compound according to claim 21 wherein n is 0.

23. A compound according to claim 22, which is L-phenylglycyl-[4-(methylsulfinyl)-D-2-aminobutanoyl]glycyl-N-(2-adamantyl)-L-phenylalaninamide.

24. A compound according to claim 21 wherein n is 1.

25. A compound according to claim 24 having the formula:

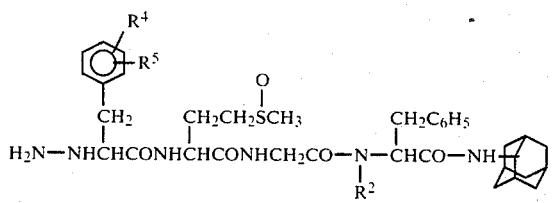

and the stereochemical configuration of each of the optically active amino acid residues may independently be D, L, or DL; and the pharmaceutically acceptable salts thereof.

26. A compound according to claim 25, which is L-phenylalanyl-[4-(methylsulfinyl)-D-2-aminobutanoyl]glycyl-N-(2-adamantyl)-L-phenylalaninamide.

27. A compound according to claim 25, which is 4-t-butyl-D,L-phenylalanyl-[4-methylsulfinyl)-D-2-aminobutanoyl]glycyl-N-(2-adamantyl)-L-phenylalaninamide.

28. A compound according to claim 25, which is 4-fluoro-D,L-phenylalanyl-[4-methylsulfinyl)-D-2-aminobutanoyl]glycyl-N-(2-adamantyl)-L-phenylalaninamide.

29. A compound according to claim 24 having the formula:

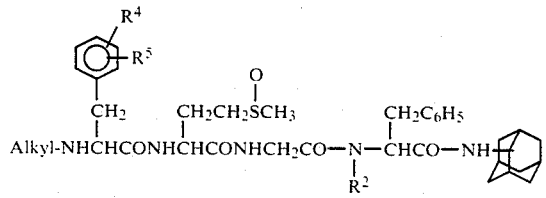

and the stereochemical configuration of each of the optically active amino acid residues may independently be D, L, or DL; and the pharmaceutically acceptable salts thereof.

30. A compound according to claim 29, which is $N^\alpha$-methyl-L-phenylalanyl-[4-methylsulfinyl)-D-2- aminobutanoyl]glycyl-N-(2-adamantyl)-L-phenylalaninamide.

31. A compound according to claim 29, which is N$^\alpha$-ethyl-L-phenylalanyl-[4-methylsulfinyl)-D-2-aminobutanoyl]glycyl-N-(2-adamantyl)-L-phenylalaninamide.

32. A compound according to claim 29, which is N$^\alpha$-ethyl-L-phenylalanyl-[4-methylsulfinyl)-D-2-aminobutanoyl]glycyl-N-(2-adamantyl)-N$^\alpha$-methyl-L-phenylalaninamide.

33. A compound according to claim 21 wherein n is 2.

34. A compound according to claim 33, which is L-2-amino-4-phenylbutanoyl-[4-methylsulfinyl)-D-2-aminobutanoyl]glycyl-N-(2-adamantyl)-L-phenylalaninamide.

35. A compound according to claim 1 having the formula:

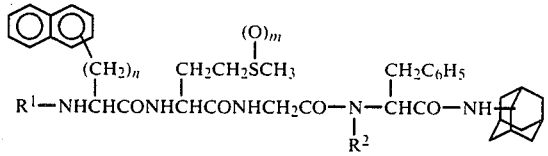

and the stereochemical configuration of each of the optically active active amino acid residues may independently be D, L, or DL; and the pharmaceutically acceptable salts thereof.

36. A compound according to claim 35 wherein n is 1.

37. A compound according to claim 36, which is 3-(2-naphthalenyl)-L-alanyl-D-methionylglycyl-N-(2-adamantyl)-L-phenylalaninamide.

38. A compound according to claim 36, which is 3-(2-naphthalenyl)-L-alanyl-[4-methylsulfinyl-D-2-aminobutanoyl]glycyl-N-(2-adamantyl)-L-phenylalaninamide.

39. A compound according to claim 1 having the formula:

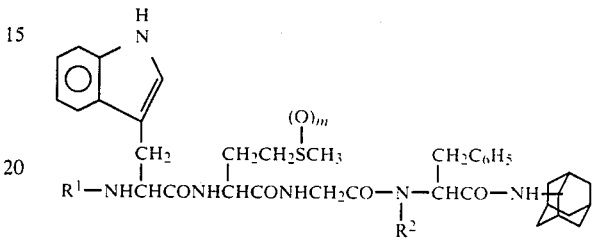

and the stereochemical configuration of each of the optically active amino acid residues may independently be D, L, or DL; and the pharmaceutically acceptable salts thereof.

40. A compound according to claim 39, which is L-tryptophanyl-D-methionylglycyl-N-(2-adamantyl)-L-phenylalaninamide.

* * * * *